United States Patent van der Aalst et al.

[11] Patent Number: 5,959,168
[45] Date of Patent: Sep. 28, 1999

[54] ZEOLITE-BASED ETHYLABENZENE PROCESS ADAPTABLE TO AN ALUMINUM CHLORIDE-BASED ETHYLBENZENE PLANT

[75] Inventors: Matheus J. M. van der Aalst; Mohammed S. U. Samson, both of Terneuzen, Netherlands; Garmt R. Meima, Midland, Mich.; Michael Q. de Steenwinkel, Philippine, Netherlands

[73] Assignee: The Dow Chemical Company, Midland, Mich.

[21] Appl. No.: 08/945,595

[22] PCT Filed: Oct. 1, 1997

[86] PCT No.: PCT/US97/17844

§ 371 Date: Feb. 17, 1998

§ 102(e) Date: Feb. 17, 1998

[87] PCT Pub. No.: WO98/14417

PCT Pub. Date: Apr. 9, 1998

Related U.S. Application Data

[63] Continuation-in-part of application No. 08/724,748, Oct. 2, 1996, abandoned.

[51] Int. Cl.[6] .............. C07C 1/00; C07C 2/64; C07C 2/68; C07C 5/22
[52] U.S. Cl. .............. 585/323; 585/313; 585/316; 585/450; 585/467; 585/475
[58] Field of Search .............. 585/323, 312, 585/316, 450, 467, 475

[56] References Cited

U.S. PATENT DOCUMENTS

| | | | |
|---|---|---|---|
| 4,358,362 | 11/1982 | Smith et al. | 208/91 |
| 4,459,426 | 7/1984 | Inwood et al. | 585/323 |
| 4,665,255 | 5/1987 | Chang et al. | 585/467 |
| 4,798,816 | 1/1989 | Ratcliffe et al. | 502/62 |
| 4,891,458 | 1/1990 | Innes et al. | 585/323 |
| 4,992,606 | 2/1991 | Kushnerick et al. | 585/467 |
| 5,004,841 | 4/1991 | Lee et al. | 568/678 |
| 5,081,323 | 1/1992 | Innes et al. | 585/449 |
| 5,145,817 | 9/1992 | Sherrod | 502/65 |
| 5,149,894 | 9/1992 | Holtermann et al. | 585/467 |
| 5,178,748 | 1/1993 | Casci et al. | 208/46 |
| 5,198,595 | 3/1993 | Lee et al. | 585/467 |
| 5,236,575 | 8/1993 | Bennett et al. | 208/46 |
| 5,243,116 | 9/1993 | Lee et al. | 585/467 |
| 5,258,565 | 11/1993 | Kresge et al. | 585/467 |
| 5,430,211 | 7/1995 | Pogue et al. | 585/323 |
| 5,453,554 | 9/1995 | Cheng et al. | 585/467 |
| 5,600,048 | 2/1997 | Cheng et al. | 585/449 |

FOREIGN PATENT DOCUMENTS

| | | |
|---|---|---|
| 0366515 A1 | 5/1990 | European Pat. Off. |
| 0537389 A1 | 4/1993 | European Pat. Off. |
| 0432814 B1 | 9/1995 | European Pat. Off. |
| WO 94/29245 | 12/1994 | WIPO |
| WO 95/11196 | 4/1995 | WIPO |

OTHER PUBLICATIONS

K. Weissermel and H.–J. Arpe, *Industrial Organic Chemistry*, 2nd ed., VCH Verlagsgesellschaft, Weinheim, Germany, 1993, pp. 333–336.

*Primary Examiner*—Glenn Caldarola
*Assistant Examiner*—Thuan D. Dang
*Attorney, Agent, or Firm*—Marie F. Zuckerman

[57] ABSTRACT

A zeolite-based ethylbenzene process which is suitable for retrofitting aluminum chloride-based ethylbenzene plants. The process involves alkylating benzene with ethylene in an alkylation zone in the presence of zeolite beta or Y or an MCM zeolite so as to produce an alkylation product mixture containing benzene, ethylbenzene, and polyethylbenzenes which can be separated in the aromatics recovery (distillation) stage of an aluminum chloride-based plant. The polyethylbenzenes are subsequently contacted with benzene in a transalkylation zone using zeolite beta or mordenite or Y so as to produce a transalkylation product mixture which is also separable in the aromatics recovery stage of an aluminum chloride-based plant.

19 Claims, 1 Drawing Sheet

5,959,168

ZEOLITE-BASED ETHYLABENZENE PROCESS ADAPTABLE TO AN ALUMINUM CHLORIDE-BASED ETHYLBENZENE PLANT

CROSS REFERENCE TO RELATED APPLICATIONS

This application claims the benefit of international application no. PCT/US97/17844, filed Oct. 1, 1997, which claims the benefit and is a continuation-in-part of application Ser. No. 08/724,748, now abandoned, filed Oct. 2, 1996.

This invention relates to a process of alkylating benzene with ethylene in the presence of a catalytic zeolite to form ethylbenzene.

Ethylbenzene is used to prepare styrene from which polystyrene is prepared.

Historically, ethylbenzene is commercially manufactured by the liquid phase alkylation of benzene with ethylene in the presence of a Friedel-Crafts catalyst, most typically aluminum chloride. Hydrogen chloride may be required as a co-catalyst. (See, for example, K. Weissermel and H.-J. Arpe, *Industrial Organic Chemistry*, 2$^{nd}$ ed., VCH Press, Weinheim, Germany, 1993, pp. 333–336.) An aluminum chloride ethylbenzene plant typically comprises a benzene drying stage, a catalyst preparation stage, an alkylation stage, a transalkylation stage, a neutralization and catalyst disposal stage, and an aromatic product recovery (distillation) stage.

As regards the alkylation stage, the selectivity to ethylbenzene is enhanced by using a high benzene/ethylene molar ratio, typically around 3:1. Nevertheless, the product mixture obtained from the alkylation contains benzene, ethylbenzene, and polyethylbenzenes including diethylbenzenes, triethylbenzenes, tetraethylbenzenes, and optionally higher polyethyl-benzenes. The alkylation product mixture is fed to a transalkylation reactor and contacted with a transalkylation catalyst, such as an aluminum chloride complex. A transalkylation product mixture is obtained having a composition close to that expected for thermodynamic equilibrium, which provides the maximum attainable ethylbenzene. The product mixture from the transalkylator, after neutralization, is separated in the aromatics recovery stage of the plant which typically comprises a three column distillation train. The first column recovers benzene which may then be recycled to the alkylation reactor or to the transalkylation reactor. The second column recovers the desired ethylbenzene end-product. The third column recovers diethylbenzenes and triethylbenzenes, and if present, higher polyethylbenzenes.

An aluminum chloride-based ethylbenzene plant has several disadvantages, among them, the corrosiveness of the alkylation catalyst and process streams. Accordingly, high investment and maintenance costs are incurred to ensure that numerous parts of the plant are corrosion resistant. In addition, the aluminum chloride catalyst, which is dissolved or suspended in the reaction mixture, must be removed from the product stream and disposed. Removal is effected by neutralization via an elaborate series of aqueous and caustic washes. Increased expenditures are required for the catalyst preparation and neutralization stages of the plant. As a further disadvantage, an aluminum-containing waste is obtained whose disposal can create significant environmental problems.

It is known that the alkylation of benzene with ethylene to form ethylbenzene can be catalyzed by a solid acid, specifically, an acidic zeolite. Many zeolites have been disclosed for alkylation, including mordenite, ZSM-5, ZSM-11, ZSM-12, Y, omega, EU-1, NU-87, beta, MCM-22, MCM-36, MCM-49, MCM-56, MCM-58, and SSZ-25. With regard to the use of dealuminated acid mordenite zeolite in the ethylation of benzene, reference is made, for example, to U.S. Pat. Nos. 5,004,841, 5,198,595, and 5,243,116. With regard to the use of zeolite ZSM-5, reference is made to U.S. Pat. No. 4,665,255. For alkylations with zeolites ZSM-11 and ZSM-12, reference is made to U.S. Pat. No. 4,358,362. With regard to the use of zeolite EU-1, reference is made for example to EP-A1 -0,537,389; for zeolite NU-87 to U.S. Pat. No. 5,178,748; for zeolite beta, reference is made, for example, to U.S. Pat. No. 4,891,458 and to U.S. Pat. No. 5,081,323; for zeolite Y to U.S. Pat. No. 4,459,426 and to U.S. Pat. No. 4,798,816 and to U.S. Pat. No. 4,876,408; for zeolite MCM-22 to U.S. Pat. No. 4,992,606; for zeolite MCM-36 to U.S. Pat. No. 5,258,565; for zeolite MCM-49 to U.S. Pat. No. 5,236,575 and PCT publication WO 94/29245; for MCM-56 to U.S. Pat. No. 5,453,554; for MCM-58 to WO 95/11196; and for SSZ-25 to U.S. Pat. No. 5,149,894.

Zeolites offer several advantages over aluminum chloride; most notably, zeolites are environmentally harmless and non-corrosive. Additionally, alkylations with zeolite catalysts do not require catalyst preparation and neutralization stages. Even more advantageously, the waste problems associated with aluminum chloride-based ethylbenzene plants are eliminated.

On the other hand, zeolite catalysts may possess different energy and feed composition requirements and may produce different isomeric and by-product mixtures from an aluminum chloride catalyst. For example, the gas phase alkylation of benzene to ethylbenzene over zeolite ZSM-5 produces xylenes as undesirable by-products. Moreover, gas phase processes typically possess higher energy levels than an aluminum chloride-based process. As another disadvantage, zeolite-based ethylbenzene plants are generally grass-roots designs which customize the benzene alkylation, transalkylation, and product recovery stages to the activity and selectivity of the zeolite employed. Such plants require a significant expenditure of capital.

It would be advantageous from an environmental and economic point of view, if an aluminum chloride-based ethylbenzene plant could be retrofitted with solid acid alkylation and transalkylation catalysts, so as to convert the plant into a zeolite-based facility. In order to obtain the increased economic advantages of a retrofit design, however, the pre-existing aromatics recovery (distillation) stage of the aluminum chloride-based plant must be essentially unmodified. This can best be accomplished, if the product mixture derived from the zeolite-based process is a close match to the product mixture derived from the aluminum chloride-based plant. Such a successful conversion of an aluminum chloride-based ethylbenzene plant into a zeolite-based ethylbenzene plant would provide the multiple benefits of zeolite catalysis at significantly reduced capital investment.

SUMMARY OF THE INVENTION

This invention is a zeolite-based ethylbenzene process which is suitable for retrofitting an aluminum chloride-based ethylbenzene plant. The process broadly comprises three stages. In the first stage, which is conducted in an alkylation zone, benzene is contacted with ethylene in at least a partial liquid phase at a total benzene/ethylene molar ratio between 1.5:1 and 3.0:1 in the presence of a catalytic amount of an alkylation catalyst selected from acidic zeolites beta, Y, MCM-22, MCM-36, MCM-49, and MCM-56. The contacting is conducted under process conditions sufficient to prepare an alkylation product mixture comprising benzene, ethylbenzene, and polyethylbenzenes, including diethylbenzenes, and higher molecular weight residues. Under the contacting conditions described herein the diethylbenzenes/ethylbenzene weight ratio in the alkylation product mixture ranges from 1:2.5 to 1:8.0.

In the second stage of the novel retrofit process of this invention, the alkylation product mixture is separated in an aromatics recovery stage designed for an aluminum chloride-based plant. Specifically, the alkylation product mixture is passed into a three-column distillation train. Benzene is recovered in the first column. Thereafter, the bottoms from the first distillation column comprising ethylbenzene, polyethylbenzenes, and higher molecular weight residues are passed into a second distillation column to recover ethylbenzene. Thereafter, the bottoms from the second distillation column comprising polyethylbenzenes and higher molecular weight residues are passed into a third distillation column to recover polyethylbenzenes including diethylbenzenes.

In the third stage of the novel retrofit process of this invention, the polyethylbenzenes which are recovered from the third distillation column are passed into a transalkylator wherein the polyethylbenzenes are contacted with benzene in the liquid phase at a molar ratio of total moles of benzene groups on the benzene and polyethylbenzenes to total moles of ethyl groups on the polyethylbenzenes ranging from 1.5:1 to 3.0:1. The contacting occurs in the presence of a catalytic amount of a transalkylation catalyst selected from acidic zeolites mordenite, beta, and Y. The contacting is conducted under reaction conditions sufficient to produce a transalkylation product mixture containing benzene, ethylbenzene, and polyethylbenzenes, including diethylbenzenes such that the weight ratio of the diethylbenzenes to ethylbenzene ranges from 1:2.5 to 1:8.0.

Finally, the transalkylation product mixture is passed into the aforementioned distillation train, and thereafter the transalkylation product mixture is separated in the three distillation columns mentioned hereinbefore to recover benzene, ethylbenzene, and polyethylbenzenes.

In an additional embodiment of this invention, the heat generated from the alkylation stage is used to operate the distillation stages and/or preheat the feedstreams of the alkylation and transalkylation stages.

The unique selection in this invention of specific solid acid alkylation catalysts with specific molar ratios of alkylation reactants produces an alkylation product mixture having a diethylbenzenes/ethylbenzene weight ratio between 1:2.5 and 1:8.0. Significantly, an alkylation product mixture of this composition is readily separated in the pre-existing distillation columns of an aluminum chloride-based ethylbenzene plant. Essentially no modification of the distillation stage is required. Likewise, the selection in this invention of specific transalkylation solid acid catalysts with specific molar ratios of transalkylation reactants gives rise to a transalkylation product mixture having a diethylbenzenes/ ethylbenzene weight ratio between 1:2.5 and 1:8.0. Here too, the separation of the transalkylation product mixture is readily adapted to the pre-existing distillation stages of an aluminum chloride-based ethylbenzene plant.

In view of the above, the process of this invention is usefully employed to convert an aluminum chloride-based ethylbenzene plant into a zeolite-based ethylbenzene plant. Zeolite catalysts eliminate the many disadvantages of an aluminum chloride catalyst. For example, zeolites are not corrosive, therefore plant maintenance costs are lower. Moreover, zeolite-based plants do not require the elaborate and expensive neutralization and waste disposal stages of aluminum chloride-based plants. Additionally, retrofitting an existing plant expends significantly less capital than installing a new plant from a grass-roots design. As a further advantage, the liquid phase zeolite-based process of this invention requires less energy input than other zeolite-based processes, and beneficially produces little or no unwanted xylenes. Finally, in the alternative embodiment of this invention wherein the heat generated from the alkylation stage is used to operate the distillation stage and preheat the alkylation and transalkylation stages, the process of this invention advantageously requires essentially zero-energy input. Such a reduction in energy input translates into further economic savings.

BRIEF DESCRIPTION OF THE DRAWING

The FIGURE is a drawing of a zeolite-based ethylbenzene plant which is suitable for retrofitting an aluminum chloride-based ethylbenzene plant.

DETAILED DESCRIPTION OF THE INVENTION

Figure 1:
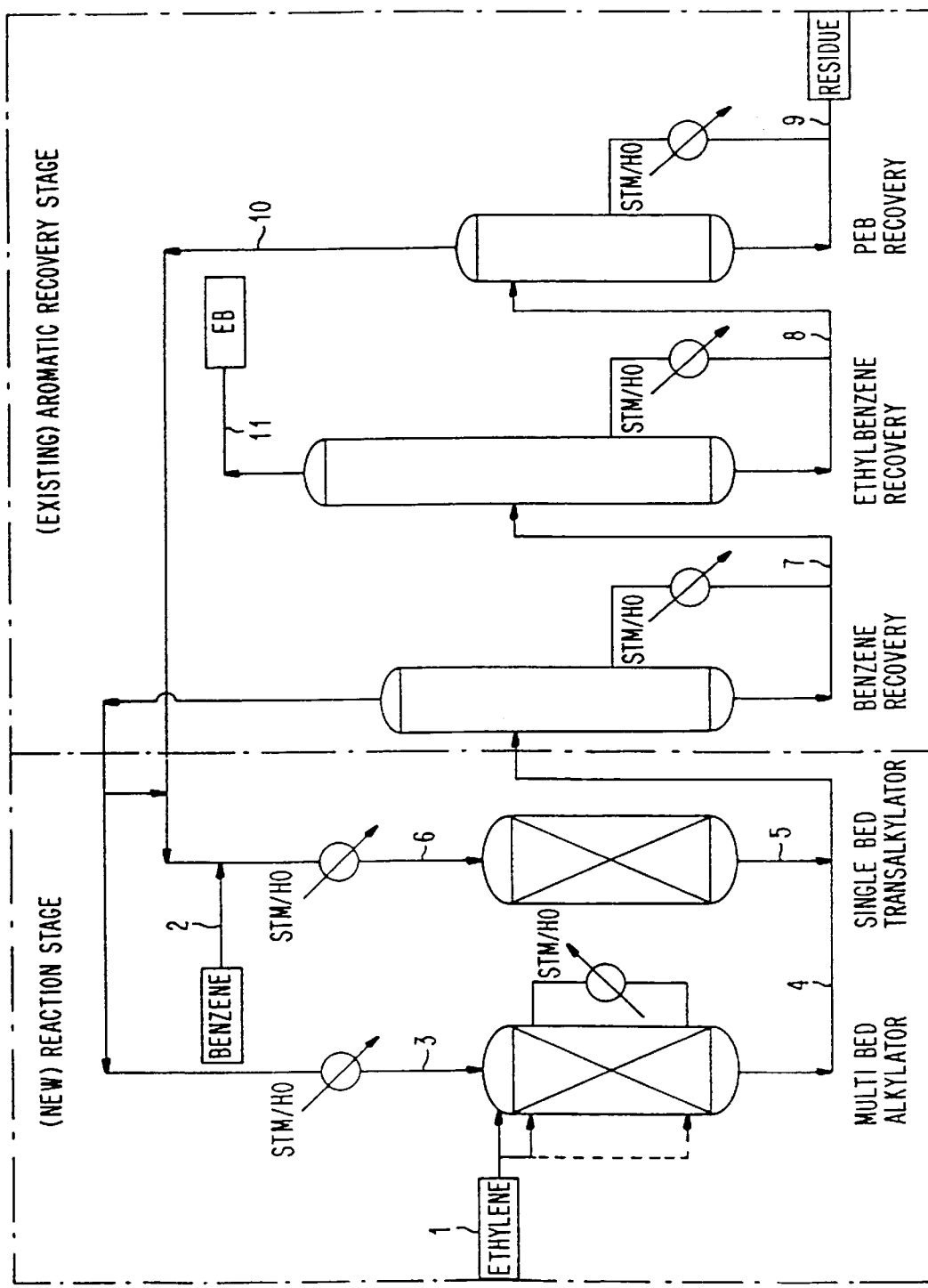

The novel invention described herein is a zeolite-based process for producing ethylbenzene which is particularly well adapted for retrofitting an aluminum chloride-based ethylbenzene plant. The process involves three stages. More particularly, the process involves the selection of specific alkylation and transalkylation catalysts and specific molar ratios of reactants so as to produce alkylation and transalkylation product streams which closely match the product streams obtained from an aluminum chloride-based process. The product streams are matched with respect to chemical composition and with respect to the relative amounts of components. As a consequence, the alkylation and transalkylation product streams derived from the process of this invention can be readily separated in the pre-existing aromatics recovery stage of an aluminum chloride-based ethylbenzene plant.

In the first stage of the novel retrofit process of this invention, fresh benzene (Feed 2, FIG. 1) or recycle benzene (Feed 3, FIG. 1) is contacted with ethylene (Feed 1, FIG. 1) in at least a partial liquid phase in an alkylation zone at a total benzene/ethylene molar ratio between 1.5:1 and 3.0:1 and in the presence of a catalytic amount of a zeolitic alkylation catalyst. Preferably, the total benzene/ethylene molar ratio varies between 1.7:1 and 2.5:1. The catalyst is selected from acidic zeolites beta, Y, MCM-22, MCM-36, MCM-49, and MCM-56. The alkylation process conditions, described in detail hereinbelow, are sufficient to prepare an alkylation product mixture containing benzene, ethylbenzene, and polyethylbenzenes including diethylbenzenes, triethylbenzenes, and optionally tetra, penta, and hexaethylbenzenes, as well as, a higher molecular weight residue. Under the conditions described herein, the diethylbenzenes/ethylbenzene weight ratio in the product mixture ranges from 1:2.5 to 1:8.0, preferably, from 1:4.0 to 1:7.0 Additionally, under the process conditions described herein the benzene/ethylbenzene weight ratio in the alkylation product typically varies from 1:1 to 2:1.

The alkylation reactor in which the benzene is contacted with the ethylene is suitably a continuous flow reactor wherein the catalyst may occupy a fixed-bed, slurry bed, or fluidized bed. Preferably, the catalyst is loaded into a fixed-bed. The alkylation reactor is beneficially designed to control the temperature close to isothermal conditions. Accordingly, the heat obtained from the exothermic alkylation reaction is removed directly by use of a shell and tube reactor design or indirectly by use of external heat exchangers.

Benzene and ethylene are required for the alkylation process and may be obtained from any commercial source. Optionally, the benzene may be dried before use, preferably, by azeotropic distillation. Alternatively, the benzene may be dried over any suitable solid drying agent selected, for example, from aluminas, silicas, silica-aluminas, and zeolites. Preferred drying agents include LTA zeolites, such as 3A, 4A, and 5A, as well as Linde brand zeolite 13X and SELEXSORB® brand activated alumina (Alcoa Industrial Chemicals). After drying, the water concentration in the benzene feed is preferably reduced to a value less than 300 parts per million (ppm) by weight, and preferably, less than 200 ppm.

Optionally, the benzene feed may be pretreated before use to remove oxygen which is capable of inhibiting the alkylation catalyst. A typical pretreatment procedure involves sparging the liquid benzene feed with an oxygen-free sparge gas or passing the benzene over a reduced copper bed, as described in U.S. Pat. No. 5,300,722.

Benzene and ethylene may be introduced into the alkylation zone as separate feeds or as a combined feed. Further, the benzene may be introduced to the alkylation zone as a single feed stream or split into a plurality of feedstreams which are introduced into the reactor at different locations. Ethylene, on the other hand, is beneficially split into a plurality of feedstreams which are introduced into the reactor at different locations. A preferred design comprises a plurality of catalyst-containing reaction zones in fluid connection in series. In this design, the entire benzene feed is delivered to the first reaction zone, while a series of fractions of ethylene is delivered respectively to the first reaction zone and between each pair of contiguous reaction zones. The reaction zones may be operated with the same or different alkylation catalysts and at the same or different temperatures and space velocities. More preferably, three to twenty catalyst-containing reaction zones are used and a corresponding number of alkylating agent streams. Increasing the number of catalyst beds augments the ethylbenzene selectivity, as compared with supplying the whole of the alkylating agent to the first reaction zone. Furthermore, by feeding the alkylating agent as a series of fractions, a better control of the reaction temperature is possible for this exothermic reaction.

The catalyst required for the alkylation stage is selected from acidic crystalline aluminosilicates beta, Y, MCM-22, MCM-36, MCM-49, and MCM-56. Zeolite beta is originally described in U.S. Pat. No. 3,308,069 and U.S. Re 28,341, and later described in U.S. Pat. Nos. 4,891,458 and 5,081,323. Zeolite Y is described in U.S. Pat. No. 3,130,007, and modified forms thereof are described in U.S. Pat. No. 4,459,426 and 4,798,816. Zeolite MCM-22 is described in U.S. Pat. No. 4,992,606. Zeolite MCM-36 is fully described in U.S. Pat. No. 5,258,565. A description of MCM-49 is found in WO 94/29245, and MCM-56 is found in U.S. Pat. No. 5,453,554. Modified forms of the aforementioned zeolites, including these zeolites as modified by acid, steam, or heat treatments or by ion-exchange or impregnation with metal ions, may also be employed. Preferably, the alkylation catalyst is acidic zeolite beta, MCM-22, or Y.

Optionally, the alkylation catalyst may be bound to, supported on, or extruded with any support material for the purpose of increasing the catalyst's strength and attrition resistance. Suitable supports include aluminas, silicas, aluminosilicates, titania, and clays. Preferably, the support is an alumina or silica.

For a continuous mode of operation, any weight hourly space velocity of the total feed with respect to the catalyst is beneficially employed which gives rise to a final alkylation product stream wherein the diethylbenzenes/ethylbenzene weight ratio ranges from 1:2.5 to 1:8.0. The exact weight hourly space velocity to be applied will depend on the intrinsic activity of the zeolite under consideration. The more active the zeolite, the shorter the residence times that can be used. Typically, the weight hourly space velocity of the total feed comprising benzene and ethylene over the total alkylation catalyst ranges from 5 grams total feed per gram catalyst per hour, or simply $hr^{-1}$, to 100 $hr^{-1}$, and preferably, from 10 $hr^{-1}$ to 20 $hr^{-1}$.

The alkylation stage of this invention is carried out at any temperature and pressure which give rise to a final alkylation product stream wherein the diethylbenzenes/ethylbenzene weight ratio ranges from 1:2.5 to 1:8.0. In addition, the reaction conditions should be sufficient to maintain at least one of the reactants or product compounds in at least partial liquid phase, or alternatively in full liquid phase, in order to retard catalyst fouling. Typically, benzene is introduced in the liquid phase. Ethylene is then supplied into each reaction zone in such a way that it dissolves into the benzene and/or other product compounds. Typically, the contacting temperature ranges between 100° C. and 300° C., preferably, between 200° C. and 265° C. The pressure should be sufficient to keep the alkylating agent substantially in solution, but not so high as to accelerate catalyst deactivation. Pressures between 10 bar gauge (barg) (1,000 kPa) and 50 barg (5,000 kPa), and preferably, between 25 barg (2,500 kPa) and 35 barg (3,500 kPa), are suitably employed.

If the alkylation stage is designed and run as described hereinabove with a total benzene/ethylene molar ratio of between 1.5:1 and 3.0:1, then ethylbenzene is typically produced in at least 65 percent selectivity. For the purposes of this invention, the ethylbenzene selectivity is defined as the mole percentage of converted benzene which forms ethylbenzene. Diethylbenzenes are also produced, primarily as the para and meta isomers. Triethylbenzenes and optionally tetraethylbenzenes, pentaethylbenzenes, and hexaethylbenzenes may also be produced. A total selectivity to mono-, di-, and triethylbenzenes of at least 95 mole percent, and preferably, at least 99.0 mole percent is achieved. These selectivities compare favorably with the selectivities found in an aluminum chloride-based ethylbenzene process.

In the second stage of the retrofit process of this invention, the alkylation product mixture is separated into its constituent parts. Separation is effected by distillation in an aromatics recovery zone which is designed for an aluminum chloride-based ethylbenzene plant. In the distillation sequence, the alkylation product stream (Feed 4, FIG. 1) is fed into a first distillation column wherein benzene (Stream 3, FIG. 1) is recovered. The recovered benzene may be, in whole or in part, recycled to the alkylation stage or fed into the transalkylation stage. Thereafter, the bottoms (Stream 7, FIG. 1) from the first distillation column comprising ethylbenzene, polyethylbenzenes, and higher molecular weight residues are passed into a second distillation column wherein substantially pure ethylbenzene (Stream 11, FIG. 1) is recovered. Subsequently, the bottoms (Stream 8, FIG. 1) from the second distillation column comprising polyethylbenzenes and higher molecular weight residues are passed into a third distillation column wherein diethylbenzenes, and optionally triethylbenzenes and tetraethylbenzenes are recovered. This third fraction (Stream 10, FIG. 1), preferably containing little or essentially no higher molecular weight residues, is fed to the transalkylation reactor. A residue (Stream 9, FIG. 1) is also recovered as bottoms from the third distillation column.

The above-described distillation train should also possess conventional design features and operational parameters suitable for the distillation of a product stream obtained from an aluminum chloride-based ethylbenzene plant. Design features include, for example, the size of the columns and the number of plates in each column. Operational parameters include, for example, column temperature, column pressure, and liquid and vapor flow rates. A variety of well-known heat sources can be used to drive the distillations, including steam, hot oils, and furnaces. Since the heat source influences the operating conditions of the distillation column, it is difficult to render a detailed description of all of the process conditions which may be operable. Generally speaking, any temperature and pressure can be employed in the distillations provided that the desired component of the product stream is separated and recovered. As a general guideline, the first distillation column which separates benzene typically operates at atmospheric pressure and at a temperature between 130° C. and 170° C. Typically, the second distillation column which separates ethylbenzene operates at a pressure of greater than 1 barg (100 kPa) up to 3 barg (300 kPa) and at a temperature between 180° C. and 240° C. Typically, the third distillation column operates at a temperature between 180° C. and 240° C. and under vacuum. The aforementioned distillation conditions are purely exemplary of the many conditions which one skilled in the art may use to separate the desired end-products. Accordingly, the process of this invention should not be limited solely to the distillation conditions mentioned herein, so long as the conditions are suitable for a product stream obtained from an aluminum chloride-based ethylbenzene plant.

In the third stage of the retrofit process of this invention, at least a portion of the polyethylbenzenes (Stream 10, FIG. 1) separated in the aromatics recovery stage is fed into a transalkylation zone wherein they are contacted with fresh benzene (Stream 2, FIG. 1) or alternatively recycle benzene (Stream 3, FIG. 1) from the benzene recovery stage in the presence of a catalytic amount of a transalkylation catalyst. The catalyst is selected from acid zeolites mordenite, beta, and Y. Zeolite mordenite is described by R. Szostak in *Handbook of Molecular Sieves: Structure, Synthesis, and Properties*, Chapman & Hall, New York, N.Y., 1992. A preferred form of mordenite zeolite is set forth in U.S. Pat. No. 5,004,841 and related U.S. Pat. Nos. 5,175,135, and 5,198,595. This preferred mordenite is an acidic mordenite having a silica/alumina molar ratio of at least 30:1 and a Symmetry Index, as determined by X-ray diffraction, of at least 1.0. The Symmetry Index is defined as the sum of the peak heights of the [111] (13.45, 2Θ) and [241] (23.17, 2Θ) reflections divided by the peak height of the [350] (26.25, 2Θ) reflection. This preferred mordenite is prepared by (1) heating a mordenite having a silica/alumina molar ratio of less than 30:1 and a Symmetry Index of between 0.5 and 1.0, and thereafter (2) treating the heated mordenite with strong acid so as to remove an amount of alumina sufficient to provide a silica/alumina molar ratio of at least 30:1, and (3) optionally, repeating the heating and strong acid treatments to remove additional alumina. Citations for zeolites beta and Y were set forth hereinbefore with respect to the alkylation catalysts. Beta, mordenite, and Y zeolites modified by acid, steam, or other treatments known to those skilled in the art may also be employed.

The transalkylation zone is generally conceived as a single catalyst bed, preferably a fixed-bed design, which operates in a continuous mode with a liquid phase reactant stream (Stream 6, FIG. 1). The polyethylbenzenes are fed into the transalkylation zone typically without any pretreatment. If the benzene is obtained from the distillation stage, then no pretreatment of the benzene is required. Alternatively, if the benzene is obtained from a fresh commercial source, then it may be desirable to pretreat the benzene as mentioned hereinabove in connection with the alkylation process. The benzene and polyethylbenzenes may be fed as a combined feed or a split feed.

Any transalkylation process conditions can be employed in the transalkylation zone provided that the transalkylation product mixture contains benzene, ethylbenzene and diethylbetzenes in a diethylbenzenes/ethylbenzene weight ratio between 1:2.5 and 1:8.0, and preferably, between 1:4.0 and 1:7.0. For example, the ratio of total moles of benzene groups in the benzene and polyethylbenzenes to total moles of ethyl groups on the polyethylbenzenes should vary from 1.5:1 to 3.0:1. Typically, the temperature ranges from 150° C. to 270° C., and preferably, from 225° C. to 250° C. Below 150° C. the catalyst activity may be too low, and the catalyst lifetime may be adversely affected. Above 270° C. the overall selectivity to ethylbenzene may decrease. Sufficient pressure is employed to keep the reactants in the liquid phase. Normally, the pressure ranges between 20 barg (2,000 kPa) and 40 barg (4,000 kPa), and preferably, between 25 barg (2,500 kPa) and 35 barg (3,500 kPa). In order to reach an acceptable level of polyethylbenzenes conversion of from 40 to 60 weight percent, the residence time of the overall transalkylation feedstream in the transalkylation zone is high resulting in a weight hourly space velocity ranging between 0.5 $hr^{-1}$ and 10 $hr^{-1}$, and preferably, between 1 $hr^{-1}$ and 3 $hr^{-1}$.

The product composition from the transalkylation stage is similar to that of the alkylation stage, both in chemical composition and relative amounts of components. Accordingly, the transalkylation product stream (Stream 5, FIG. 1) is fed together with the alkylation product stream into the aromatics recovery stage, described hereinabove, which is designed for an aluminum chloride-based ethylbenzene plant. Specifically, the transalkylation product mixture is fed into the first distillation column where benzene is recovered. The bottoms from the first distillation column containing ethylbenzene and polyethylbenzenes are fed into the second distillation column where ethylbenzene is recovered; and the bottoms from the second distillation column are fed into the third distillation column wherein polyethylbenzenes are recovered.

It is noted that the distillation stages and the preheating of the alkylation and transalkylation stages of the process of this invention require a source of heat, whereas the alkylation stage, which involves an exothermic reaction, produces heat. Accordingly, in an alternative embodiment of this invention, the design of this process can incorporate a means for transferring the heat produced from the alkylation stage to the distillation stages and/or the preheating of the alkylation and transalkylation stages, including for example, steam generation or conventional heat transfer fluids or a shell and tube reactor design. When the heat from the alkylation stage is used to drive the distillation stages of this process and preheat the feedstreams of the alkylation and transalkylation stages of this process, and when the three stages of the process are run in accordance with the preferred reaction conditions described hereinabove, then the retrofit process of this invention advantageously requires essentially zero-energy input. Only small amounts of energy may be needed to run peripheral machinery, such as the compressors and pumps.

This invention will be further clarified by a consideration of the following examples which are intended to be purely exemplary of the use of the invention. Other embodiments of the invention will be apparent to those skilled in the art from a consideration of this specification and from the practice of the invention as disclosed herein. Unless otherwise noted, all percentages are given on a weight percent basis.

COMPARATIVE EXPERIMENT 1

Alkylation with Aluminum Chloride Catalyst

For comparative purposes with the examples, the alkylation of benzene with ethylene was conducted under conventional conditions with an aluminum chloride catalyst. A homogeneous alkylator was used at 170° C. and 6 barg (600 kPa) pressure. Catalyst provided 200 ppm aluminum to the reaction. Benzene was dried in an azeotropic distillation section, but not treated further. Process conditions and results are set forth in Tables I and II.

EXAMPLE 1

Alkylation with Zeolite Beta Catalyst

Benzene was alkylated with ethylene in the presence of acidic zeolite beta to ethylbenzene. The beta zeolite (10 g, PQ Zeolites B.V., CP861 DL-25) having a $SiO_2/Al_2O_3$ molar ratio of 24 and bound with alumina (20 percent) was loaded into a continuous flow, fixed-bed tubular reactor (90 cm length×18.9 mm internal diameter) with benzene and split ethylene feeds (15 splits). The reactor was filled with carborundum (SiC) at the bottom and top, with catalyst (25 g) located in-between the carborundum layers. The benzene feedstock was dried over activated alumina (30 g SELEX-SORB® CDO brand, Alcoa) and thereafter passed over a reduced copper bed (140 g, Cu-filter R-311, BASF) to remove oxygen. A variety of benzene/ethylene molar ratios was tested between 1.5:1 and 2.5:1, as shown in Table I. Liquid phase reaction conditions were maintained. Products were analyzed by on-line gas chromatography. The reaction conditions, product distribution, and diethylbenzenes/ ethylbenzene weight ratio are set forth in Table I. Product selectivities are set forth in Table II.

When the results of Example 1 are compared with the results of Comparative Experiment 1, it is seen that the zeolite beta catalyst produces an alkylation product stream

TABLE I

Alkylation of Benzene with Ethylene as a Function of Catalyst and Benzene/Ethylene Molar Ratio

| Ex.: | CE 1 | | Ex 2 MCM-22 | | | Ex 1 Beta | | | |
|---|---|---|---|---|---|---|---|---|---|
| Catalyst: | AlCl$_3$ | | | | | | | | |
| Bz/Eth$^a$ | 2.0 | 2.4 | 1.9 | 1.5 | 1.9 | 2.0 | 2.2 | 2.4 | 2.5 |
| T (°C.) | 170 | 170 | 225 | 225 | 225 | 225 | 225 | 225 | 225 |
| P bar | 6 | 6 | 47 | 47 | 47 | 47 | 47 | 47 | 47 |
| (kPa) | 600 | 600 | 4700 | 4700 | 4700 | 4700 | 4700 | 4700 | 4700 |
| WHSV (hr$^{-1}$) | — | — | 5 | 5 | 5 | 5 | 5 | 5 | 5 |
| Bz$^b$ | 48.5 | 56.7 | 46.3 | 37.3 | 47.3 | 49.2 | 53.1 | 55.0 | 57.2 |
| EB$^b$ | 40.2 | 32.8 | 42.4 | 45.0 | 40.9 | 40.0 | 37.9 | 36.7 | 35.4 |
| DEB$^b$ | 9.9 | 9.2 | 9.8 | 14.8 | 10.2 | 9.4 | 8.0 | 7.3 | 6.6 |
| TEB$^b$ | 0.5 | 0.8 | 1.1 | 2.0 | 1.2 | 1.0 | 0.8 | 0.7 | 0.6 |
| Others$^b$ | 0.5 | 0.2 | 0.1 | 0.3 | 0.1 | 0.1 | 0.0 | 0.0 | 0.0 |
| Heavies | 0.5 | 0.3 | 0.2 | 0.5 | 0.3 | 0.2 | 0.2 | 0.2 | 0.2 |
| DEB/EB$^b$ | 1:4.1 | 1:3.6 | 1:4.3 | 1:3.0 | 1:4.0 | 1/4.3 | 1/4.7 | 1/5.0 | 1/5.4 |

$^a$Bz/Eth = benzene/ethylene molar ratio.
$^b$Weight percentage in product stream: Bz = benzene; EB = ethylbenzene; DEB = diethylbenzenes; TEB = triethylbenzenes; Others = Balance other products, excluding heavies. DEB/EB = weight ratio of diethylbenzenes to ethylbenzene.

The product selectivities, calculated as mole percentages, are set forth in Table II.

TABLE II

Product Selectivities as a Function of Catalyst$^a$

| Sel.$^b$ (mole %) | CE 1 AlCl$_3$ | Ex. 1 Beta | Ex. 2 MCM-22 |
|---|---|---|---|
| EB | 82.2 | 82.8 | 82.9 |
| DEB | 16.0 | 15.4 | 15.3 |
| TEB | 0.6 | 1.4 | 1.4 |
| Total EB + PolyEB's | 98.8 | 99.6 | 99.6 |

$^a$Product selectivities as mole percentages based on data in Table 1 for Bz/Eth ratio of 2.0 (1.9 for MCM-22).
$^b$EB = ethylbenzene; DEB = diethylbenzenes; TEB = triethylbenzenes; PolyEB's = polyethylbenzenes.

which is closely similar to the product stream produced by the aluminum chloride catalyst. Accordingly, the alkylation product stream from the beta-based process can be separated in the aromatics recovery (distillation) stage of the aluminum chloride-based plant without modification of the recovery stage.

EXAMPLE 2

Alkylation with Zeolite MCM-22 Catalyst

The alkylation of benzene with ethylene was conducted as described in Example 1 with the exception that acid zeolite MCM-22 (10 g) was used in place of zeolite beta. MCM-22 was prepared according to the method described in U.S. Pat. No. 5,334,795. Alkylation results are set forth in Tables I and II. When these results were compared with the results of Comparative Experiment 1, it was seen that zeolite MCM-22 produced an alkylation product stream which was closely similar to the product stream produced by the aluminum chloride catalyst. Accordingly, the alkylation product stream from the MCM-22-based process could be separated in the aromatics recovery (distillation) stage of the aluminum chloride-based plant without modification of the plant.

COMPARATIVE EXPERIMENT 2

Transalkylation with Aluminum Chloride Catalyst

The transalkylation of polyethylbenzenes with benzene was conducted under conventional conditions with an excess of aluminum chloride complex at 60° C. and atmospheric pressure. A heterogeneous transalkylator was used with a separate aluminum chloride complex phase. The polyethylbenzenes feedstock containing mainly diethylbenzenes was obtained from the alkylation of benzene with ethylene over a zeolite beta catalyst. Benzene feedstock was dried in an azeotropic distillation section, but not treated further. Product distribution obtained was close to 95 percent of equilibrium. Process conditions and results are set forth in Table III

TABLE III

Product Distribution in Transalkylation of Benzene with Diethylbenzenes

|  | Feedstream Composition | CE 2 AlCl$_3$ | Ex. 3$^a$ Mordenite (100 g) | Ex. 4$^b$ Beta (40 g) |
|---|---|---|---|---|
| Bz$^c$ | 66.4 | 54.4 | 54.8 | 54.8 |
| EB$^c$ | 2.1 | 37.4 | 32.4 | 32.4 |
| DEB$^c$ | 30.6 | 8.5 | 11.5 | 11.5 |
| TEB$^c$ | 0.0 | 0.3 | 0.2 | 0.4 |
| Others$^c$ | 0.9 | 0.4 | 1.1 | 0.9 |
| DEB/EB$^c$ | — | 1:4.4 | 1:2.8 | 1:2.8 |
| DEB Conv$^d$ | — | 72.2 | 62.4 | 62.4 |

$^a$T = 245° C.; P = 35 bar (3,500 kPa); WHSV = 2 hr$^{-1}$; Bz/Eth = 2.3.
$^b$T = 220° C.; P = 35 bar (3,500 kPa); WHSV = 2 hr$^{-1}$; Bz/Eth = 2.3.
$^c$Weight percentage of component in stream: Bz = benzene; EB = ethylbenzene; DEB = diethylbenzenes; TEB = triethylbenzenes; Others = Balance of products. DEB/EB = diethylbenzenes/-ethylbenzene weight ratio.
$^d$Diethylbenzenes conversion given as mole percentage.

EXAMPLE 3

Transalkylation with Zeolite Mordenite Catalyst

Mordenite zeolite was evaluated as a catalyst in the transalkylation of benzene with diethylbenzenes. The transalkylation reactor was a continuous flow, fixed bed, tubular reactor (90 cm length by 18.9 mm internal diameter) operating in an upflow mode. The reactor was filled with carborundum (SiC) at the bottom and top with catalyst located in-between the carborundum layers. An acidic mordenite zeolite having a SiO$_2$/Al$_2$O$_3$ molar ratio of 81 was prepared according to the procedure described in U.S. Pat. No. 5,175,135 and then bound with silica (20 percent, based on weight of mordenite). The bound catalyst was in the form of extrudates (3 mm) having a surface area of 355 m$^2$/g. The polyethylbenzenes feedstock containing mainly diethylbenzenes was obtained from the alkylation of benzene with ethylene over a zeolite beta catalyst. The benzene feedstock was dried over activated alumina (30 g Selexsorb CDO brand, Alcoa) and pretreated over a reduced copper bed (140 g, Cu-filter R-311, BASF) to remove oxygen. Process conditions, feedstock and product compositions are set forth in Table III. When the results of Comparative Experiment CE 2 are compared with the results of Example 3, it is concluded that the mordenite-based transalkylation produces a product composition similar enough to the composition obtained with aluminum chloride, such that the mordenite-based product can be separated in the aromatics recovery stage of an aluminum chloride-based plant.

EXAMPLE 4

Transalkylation with Beta Catalyst

Benzene was transalkylated with diethylbenzenes according to the procedure of Example 3, with the exception that the transalkylation catalyst was zeolite beta having an SiO$_2$/Al$_2$O$_3$ molar ratio of 24 (PQ Zeolite B.V., CP861 DL-25). The beta zeolite was extruded with an alumina binder (20 percent, based on weight of beta) into particles of 1.6 mm diameter having a surface area of 441 m$^2$/g. Process conditions and results are set forth in Table III. When the results of Comparative Experiment CE 2 were compared with the results of Example 4, it was concluded that the beta-based transalkylation produced a product composition similar to the composition obtained with aluminum chloride, such that the beta-based product could be separated in the aromatics recovery stage of an aluminum chloride-based plant.

We claim:

1. A zeolite-based process for producing ethylbenzene which is suitable for retrofitting an aluminum chloride-based ethylbenzene plant comprising:

(A) contacting benzene with ethylene in at least a partial liquid phase in an alkylation reactor at a total benzene/ ethylene molar ratio between 1.5:1 and 3.0:1 in the presence of a catalytic amount of an alkylation catalyst selected from acidic zeolites beta, Y, MCM-22, MCM-36, MCM-49, and MCM-56, the alkylation process conditions being sufficient to prepare an alkylation product mixture containing benzene, ethylbenzene, polyethylbenzenes including diethylbenzenes, and higher molecular weight residues, the diethylbenzenes/ ethylbenzene weight ratio ranging from 1:2.5 to 1:8.0;

(B) passing the alkylation product mixture into a distillation train designed for an aluminum-chloride based ethylbenzene plant wherein benzene is recovered in a first distillation column; thereafter passing the bottoms from the first distillation column comprising ethylbenzene, polyethylbenzenes, and higher molecular weight residues into a second distillation column to recover ethylbenzene; and thereafter passing the bottoms from the second distillation column comprising polyethylbenzenes and higher molecular weight residues into a third distillation column to recover polyethylbenzenes including diethylbenzenes;

(C) passing at least a portion of the polyethylbenzenes recovered from the third distillation column into a transalkylator wherein the polyethylbenzenes are contacted with benzene in the liquid phase at a molar ratio of total moles of benzenes in the benzene and polyethylbenzenes to total moles of ethyl groups on the polyethylbenzenes ranging from 1.5:1 to 3.0:1 in the presence of a catalytic amount of a transalkylation catalyst selected from acid zeolites mordenite, beta, and Y, the contacting being conducted under reaction conditions sufficient to produce a transalkylation product mixture containing benzene, ethylbenzene, and polyethylbenzenes including diethylbenzenes, the diethylbenzenes/ ethylbenzene weight ratio ranging from 1:2.5 to 1:8.0; and (D) passing the transalkylation product mixture into the aforementioned distillation train wherein the transalkylation product mixture is separated in the three distillation columns mentioned hereinbefore to recover benzene, ethylbenzene, and polyethylbenzenes.

2. The process of claim 1 wherein the alkylation is conducted at a temperature ranging from 100° C. to 300° C.

3. The process of claim 1 wherein the alkylation is conducted at a pressure between 10 barg (1,000 kPa) and 50 barg (5,000 kPa).

4. The process of claim 1 wherein the alkylation is conducted at a weight hourly space velocity of the total alkylation feed containing benzene and ethylene over total alkylation catalyst ranging from 5 hr$^{-1}$ to 100 hr$^{-1}$.

5. The process of claim 1 wherein the total benzene to ethylene molar ratio ranges from 1.7:1 to 2.5:1.

6. The process of claim 1 wherein the alkylation catalyst is zeolite beta or zeolite MCM-22.

7. The process of claim 1 wherein the alkylation catalyst is supported on silica or alumina.

8. The process of claim 1 wherein a plurality of catalyst-containing reaction zones in fluid connection in series is employed as the alkylation zone, wherein the whole of the benzene is delivered to a first reaction zone, and a series of fractions of ethylene are delivered respectively to the first reaction zone and between each pair of contiguous reaction zones.

9. The process of claim 8 wherein 3 to 20 catalyst-containing reaction zones are used with a corresponding number of alkylating agent streams.

10. The process of claim 1 wherein benzene is recovered from a distillation column operating at atmospheric pressure and at a temperature between 130° C. and 170° C.

11. The process of claim 1 wherein ethylbenzene is recovered from a distillation column operating at a temperature between 180° C. and 240° C. and at a pressure of 1 barg (100 kPa) to 3 barg (300 kPa).

12. The process of claim 1 wherein polyethylbenzenes are recovered in a distillation column operating under vacuum at a temperature between 180° C. and 240° C.

13. The process of claim 1 wherein the transalkylation is conducted at a temperature ranging from 150° C. to 270° C.

14. The process of claim 1 wherein the transalkylation is conducted at a pressure ranging from 20 barg (2,000 kPa) to 40 barg (4,000 kPa).

15. The process of claim 1 wherein the transalkylation is conducted at a weight hourly space velocity of the total transalkylation feedstream containing benzene and polyethylbenzenes over the transalkylation catalyst from 0.5 hr$^{-1}$ to 10 hr$^{-1}$.

16. The process of claim 1 wherein the transalkylation catalyst is zeolite beta.

17. The process of claim 1 wherein the heat generated from the alkylation stage is used to operate the distillation stages and/or preheat the feedstreams of the alkylation and transalkylation stages.

18. The process of claim 1 wherein the benzene to ethylbenzene weight ratio in the alkylation product mixture ranges from 1:1 to 2:1.

19. A zeolite-based process for producing ethylbenzene which is suitable for retrofitting an aluminum chloride-based ethylbenzene plant comprising:

(A) contacting benzene with ethylene in at least a partial liquid phase in an alkylation zone at a total benzene/ethylene molar ratio between 1.7:1 and 2.5:1 in the presence of an alkylation catalyst selected from acidic zeolites beta, Y, MCM-22, MCM-36, MCM-49, and MCM-56, the process being conducted at a temperature between 200° C. and 265° C., a pressure between 25 barg (2,500 kPa) and 35 barg (3,500 kPa), and a weight hourly space velocity of the total feed containing benzene and ethylene over total alkylation catalyst of from 10 hr$^{-1}$ to 20 hr$^{-1}$, so as to prepare an alkylation product mixture containing benzene, ethylbenzene, and polyethylbenzenes including diethylbenzenes, and higher molecular weight residues, the diethylbenzenes/ethylbenzene weight ratio ranging from 1:2.5 to 1:8.0;

(B) passing the alkylation product stream into a distillation train designed for an aluminum chloride-based ethylbenzene plant, wherein benzene is recovered in a first distillation column; thereafter passing the bottoms from the first distillation column comprising ethylbenzene, polyethylbenzenes, and higher molecular weight residues into a second distillation column to recover ethylbenzene; and thereafter passing the bottoms from the second distillation column comprising polyethylbenzenes and higher molecular weight residues into a third distillation column to recover polyethylbenzenes;

(C) passing the polyethylbenzenes recovered from the third distillation column into a transalkylator wherein the polyethylbenzenes are contacted with benzene in the liquid phase at a molar ratio of total moles of benzenes in the benzene and polyethylbenzenes to total moles of ethyl groups on the polyethylbenzenes ranging from 1.5:1 to 3.0:1 in the presence of a transalkylation catalyst selected from acidic zeolites mordenite, beta, and Y, the contacting being conducted at a temperature between 225° C. and 250° C., a pressure between 25 barg (2,500 kPa) and 35 barg (3,500 kPa), and a weight hourly space velocity of the total feed containing benzene and polyethylbenzenes over transalkylation catalyst of between 1 hr$^{-1}$ and 3 hr$^{-1}$, so as to produce a transalkylation product mixture of benzene, ethylbenzene, and polyethylbenzenes including diethylbenzenes, wherein the weight ratio of diethylbenzenes to ethylbenzene ranges from 1:2.5 to 1:8.0;

(D) feeding the transalkylation product mixture into the aforementioned distillation train wherein the transalkylation product mixture is separated in the three distillation columns mentioned hereinbefore to recover benzene, ethylbenzene, and polyethylbenzenes; and (E) optionally, using the heat generated in the alkylation reactor to operate the distillation stages and preheat the feedstreams of the alkylation and transalkylation stages.

* * * * *